(12) United States Patent
Lawes et al.

(10) Patent No.: US 6,197,032 B1
(45) Date of Patent: Mar. 6, 2001

(54) GAUGE FOR MEASURING THE PROFILE OF BONE OPENINGS

(75) Inventors: Peter Lawes, Maidenhead; Robin S. M. Ling, Dittisham, both of (GB)

(73) Assignee: Howmedica International Inc. (IE)

( * ) Notice: Subject to any disclaimer, the term of this patent is extended or adjusted under 35 U.S.C. 154(b) by 0 days.

(21) Appl. No.: 09/025,679

(22) Filed: Feb. 19, 1998

(30) Foreign Application Priority Data

Feb. 19, 1997 (GB) .................................................. 9703421

(51) Int. Cl.⁷ ...................................................... A61B 17/58
(52) U.S. Cl. .................................................. 606/91; 606/100
(58) Field of Search .................. 606/53–55, 91, 606/99, 100; 623/18, 22, 23; 33/533, 501, 178; 600/587, 590, 591, 594

(56) References Cited

U.S. PATENT DOCUMENTS

| | | | |
|---|---|---|---|
| 2,309,270 | * | 1/1943 | Opotow ..................................... 32/19 |
| 2,759,271 | | 8/1956 | Von Duyke . |
| 3,945,122 | * | 3/1976 | Durand et al. .......................... 33/174 |
| 4,433,686 | * | 2/1984 | Charnley ................................. 623/22 |
| 4,444,204 | | 4/1984 | Bryant et al. . |
| 4,936,856 | | 6/1990 | Keller . |
| 4,987,904 | | 1/1991 | Wilson . |
| 5,007,936 | | 4/1991 | Woolson . |
| 5,070,623 | | 12/1991 | Barnes . |

FOREIGN PATENT DOCUMENTS

| | | | |
|---|---|---|---|
| 37 05718 A1 | 9/1988 | (DE) . | |
| 43 42 971 C1 | 2/1995 | (DE) . | |
| 650707 | * | 3/1995 | (EP) ........................................ 606/91 |
| 0 650 706 A1 | 5/1995 | (EP) . | |
| 0 650 707 A1 | 5/1995 | (EP) . | |

* cited by examiner

Primary Examiner—Michael Buiz
Assistant Examiner—Lien Ngo
(74) Attorney, Agent, or Firm—Lerner, David, Littenberg, Krumholz & Mentlik, LLP

(57) ABSTRACT

A profile gauge for use with an acetabular cup loading tube provided with a skirt or flange characterized by adjustable means for measuring and indicating the diametric profile of the mouth of the rim area adjacent thereto of an acetabular socket into which an acetabular cup is to be implanted and includes means for removably locating said adjustable means on a loading tube to indicate on the skirt thereof the measured diameter profile.

16 Claims, 5 Drawing Sheets

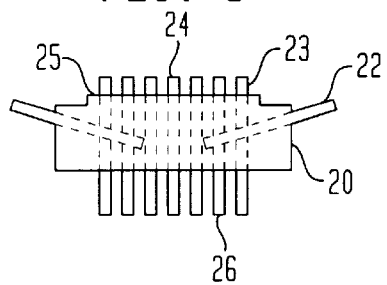
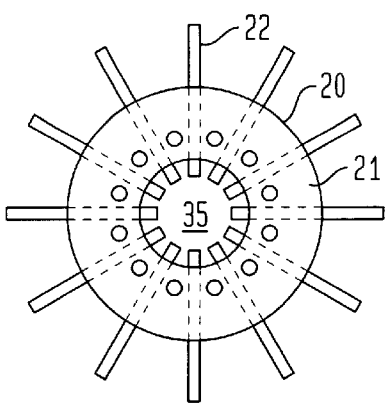
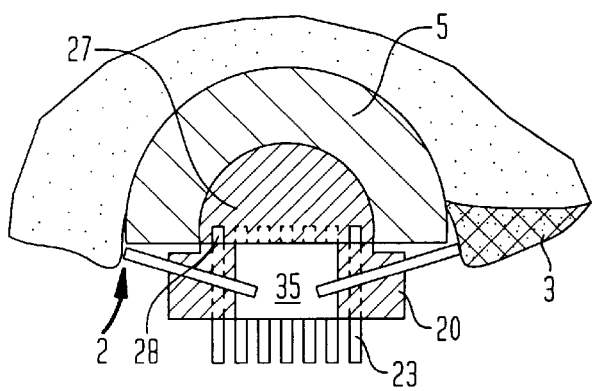
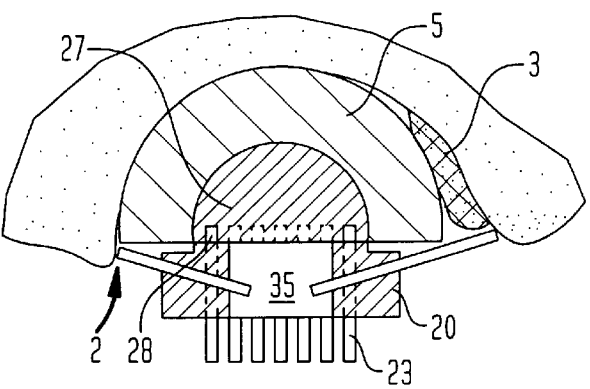
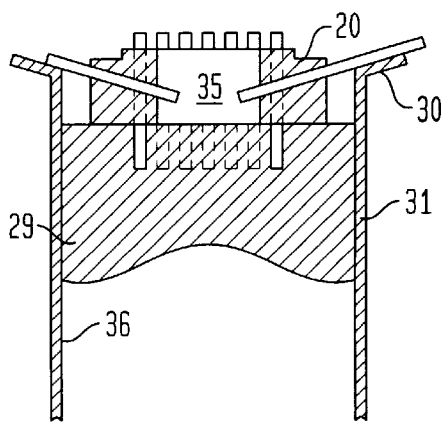

GAUGE FOR MEASURING THE PROFILE OF BONE OPENINGS

BACKGROUND OF THE INVENTION

1. Field of the Invention

This invention relates to a profile gauge for measuring and indicating the diametric profile of a bone opening and is particularly, although not exclusively, applicable for use with an acetabular cup loading tube which is provided with a skirt.

2. Description of the Prior Art

In certain surgical operations it is convenient to be able to measure the diametric profile of a bone opening, for example, if a plate of specific size is to be used or if an acetabular cup is to be implanted into an acetabular socket.

U.S. Pat. No. 5,527,317 shows an apparatus for implanting an acetabular cup employing a loading tube adapted for alignment with an acetabular socket. The bore of the tube being dimensioned to receive an acetabular cup as a sliding fit to guide it into the socket and the present invention can provide a profile gauge which can be used with such a loading tube.

If a rim cutter is used to produce a step inside the bony rim of a natural acetabulum, two problems can arise. Firstly it demands a very high level of surgeon patience, care, calmness, experience, determination and skill to position the cutter accurately and hold it on course. Otherwise, the cutter can cut eccentrically and find its own orientation. Secondly, many acetabulae are insufficiently circular to allow the rim cutter to prepare a ledge around much more than about 180° and this does not permit a loading tube to seat and seal.

Furthermore, where in revision surgery, bone chips are used to reform the acetabulum the rim cutter cannot cut the recess in a bed of loose morsels of bone. Sometimes a bone graft is contained in a surgeon formed metal mesh which in turn can be anchored by bone screws. With this arrangement a rim cutter must not be used to cut this metal mesh inside the patient.

In order to overcome the difficulties, the proposed solution for both non-circular and bone chip acetabular rims is to avoid the rim cutting operation and to trim the skirt of the loading tube so that it accurately fits the bony (or grafted) acetabular rim. Thus the skirt can be trimmed to fit either within the rim or around it.

SUMMARY OF THE INVENTION

According to one object of the present invention, a profile gauge for use with an acetabular cup loading tube provided with a skirt comprises adjustable elements for measuring and indicating the diametric profile of the mouth of the rim area adjacent thereto of an acetabular socket into which an acetabular cup is to be implanted. The gauge includes a device for removably locating the adjustable elements on a loading tube to indicate on the skirt thereof the measured diameter profile.

Thus the profile gauge is used to measure the socket and the measurement can be transferred accurately to the skirt of the loading tube. Preferably, the adjustable elements include a body portion and a number of peripherally projecting indicators which can be adjusted to define the shape of the mouth of the socket. The indicators can thus be provided by axially movable pins and these can be held in place by friction between each pin and the body portion.

The body portion can be substantially annular, the indicators projecting outwardly from the periphery thereof and also inwardly into the central opening. Preferably, the device for removably locating the adjustable elements includes a plug adapted to engage and fit within the bore of the loading tube with which the gauge is to be used and said plug can be removable from the adjustable elements. The gauge can be provided with a positioning rod for axially locating it in relation to the mouth of the socket to be measured.

Thus the positioning rod can include a trial cup and can include a cup plug which can be located on or in the trial cup and to which the adjustable elements are connected. The connection between the cup plug and the adjustable elements can be detachable. In a preferred construction, the projecting indicators have a dished configuration adapted to be substantially parallel to the projecting angle of the skirt on the loading tube with which they are to be used.

According to another object of the present invention a profile gauge for measuring and indicating the diametric profile of a bone opening or the rim area adjacent thereto comprises a body portion and a number of peripherally projecting indicators which can be adjusted to define the profile or the rim area adjacent thereto of the opening in the bone to be measured.

Thus, with this construction, the general arrangement can be similar to that set forth above with or without means for locating the adjustable means in the bone opening to be measured.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 8 is a side elevation of a profile gauge according to the present invention and which can be used in the operation for installing the cup;

FIG. 9 is a plan view of the profile gauge shown in FIG. 8;

FIG. 10 is a cross-sectional side elevation showing how the profile gauge shown in FIGS. 8 and 9 can be used for measuring the profile of an acetabular socket;

FIG. 11 is a view similar to FIG. 10 showing an alternative use of the profile gauge;

FIG. 12 is a cross-sectional side elevation showing how the profile gauge shown in FIGS. 8 and 9 can be used to transfer the profile shape to the skirt of a loading tube;

DESCRIPTION OF THE PREFERRED EMBODIMENTS

Figure 1:
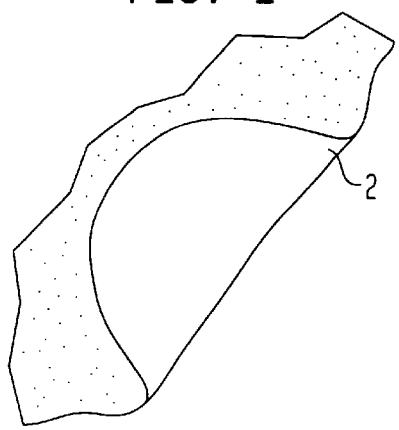
FIG. 1 is a diagrammatic cross-sectional view showing an idealized acetabular form.
Figure 2:
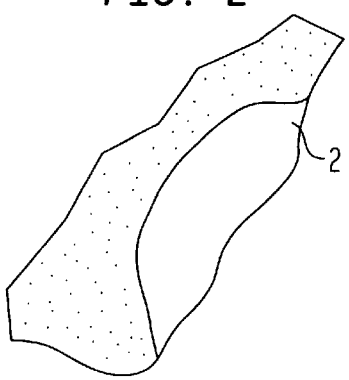
FIG. 2 is a similar view showing an eroded acetabular form.

As shown in FIG. 1, an idealized acetabular socket is substantially symmetrical and it is substantially regular around the periphery of its rim although medially there is always a substantial departure from this regularity (not shown in FIG. 1). FIG. 2 shows how the rim 2 can become eroded.

Figure 3:
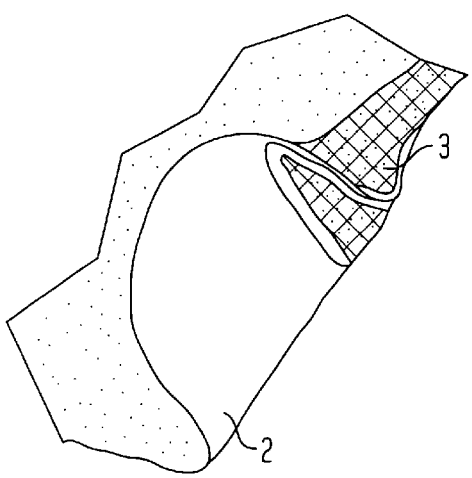
FIG. 3 is a similar view showing a reconstructed acetabular form.
Figure 4:
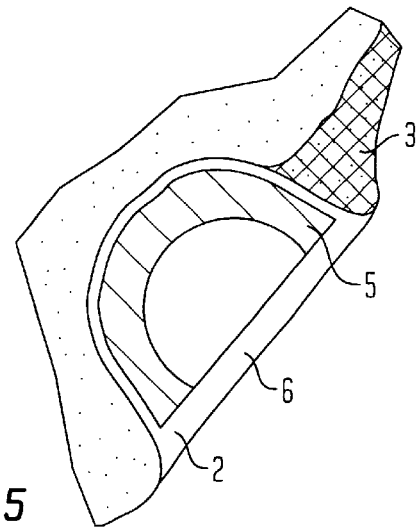
FIG. 4 is a diagrammatic view showing the employment of an oversized trial cup.

FIG. 3 shows how a surgeon can build up the rim by the use of, for example, morselized bone grafting indicated by reference number 3. The reconstruction of the acetabular forms often includes the use of metal mesh which is frequently anchored using bone screws, but no bone screws are shown in the drawing.

When an acetabular cup is to be inserted into an eroded acetabular socket as shown in FIG. 2, the surgeon first prepares the acetabulum with or without morselized bone grafting depending upon the precise state of the socket. Although the socket may be eroded, it might be possible to insert a prosthetic cup with bone grafting. An oversized trial acetabular cup 5 is placed into the prepared acetabulum 6. This trial cup is oversized to allow for the thickness of the cement mantle.

Figure 5:
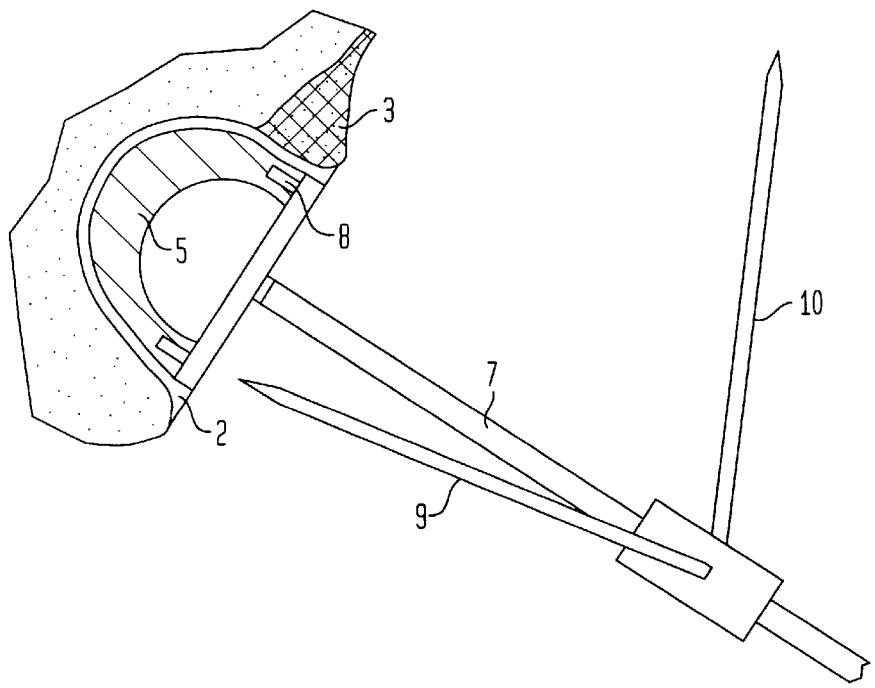
FIG. 5 is a similar diagrammatic view showing the use of orientation alignment pointers.

The trial cup can now be orientated and fitted in the pelvis to check for position and angulation and to perform a trial reduction of the hip, using an acetabular cup, rod or inserter 7 as shown in FIG. 5 which can be fitted, for example, by means of pegs 8 or other suitable means, to the trial cup 5 and carrying vertical and horizontal pointers 9 and 10. This type of adjustable pointer is well known in the industry and will not therefore be described further.

A profile gauge 20, as shown in FIGS. 8 and 9, and which will be described in more detail hereunder, can now be used in the manner described with regard to FIGS. 10 and 11 to accurately measure the rim 2 of the socket.

Where there is morselized bone grafting, the profile gauge can be used to measure beyond the bone chips and record the profile of the hard bony rim rather than that inside the graft. The profile gauge 20 and trial acetabular cup 5 are now removed from the patient. The profile gauge is attached to the skirt 30 of a loading tube 31 and the skirt is trimmed to match the profile of the acetabulum. In the arrangement shown in FIG. 11 the flange is an integral part of the loading tube, but it can be separate so that it can be assembled to the tube by the surgeon.

Figure 6:
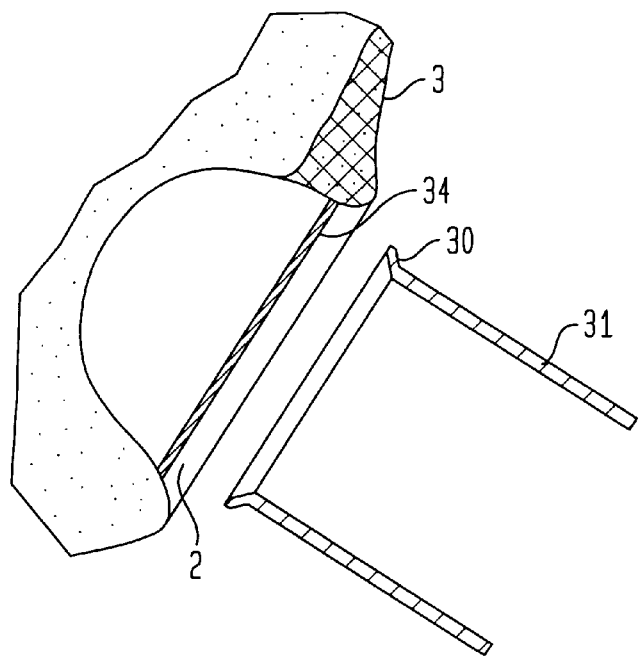
FIG. 6 is a similar view showing how the socket can be marked.
Figure 7:
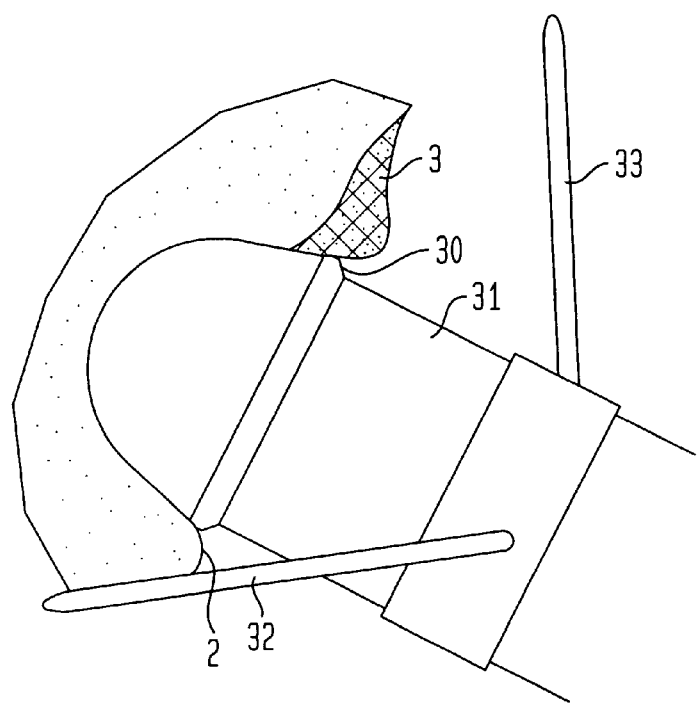
FIG. 7 shows how orientation alignment pointers can be used on a loading tube.

The loading tube 31 and skirt 30 are now fitted to the acetabulum as shown in FIG. 7 and pointers 32 and 33 mounted on the tube 31 are used to copy the chosen orientation as determined by the pointers 9 and 10 and as shown in FIG. 5. Alternatively, the acetabulum can be marked, for example with methylene blue, a commonly used marker, as shown by reference numeral 34 in FIG. 6, to shown the depth of the flange at several points around the rim 2.

The flange can thus be arranged to sit inside the bone grafting (if present) as shown in FIG. 7 leaving it exposed or it can be arranged to overlay the bone grafting and allow cement to pass under the flange but cover the graft.

The cup is now inserted in the manner described in U.S. Pat. No. 5,527,317, that is the prepared acetabulum is filled with cement through the tube 31, the cement being pushed into place by a manually operated inserter in the form of a piston (not shown in the drawings of the present invention). The piston is removed when the cement is partially set at an adequately "doughy" stage. The cup to be inserted is immediately passed down the tube by the same or a different inserter and thus the cement is pressurized from the moment the cup touches it, or the cement may need to first flow to exclude all air spaces before pressurization occurs.

A cement flow release arrangement can be provided by the provision of an orifice (not shown) in the skirt 30. The hole in the skirt is occluded, for example by the surgeon's thumb. to thus allow the pressure to build up and then allow excess cement to escape.

With the cup in place and the cement fully cured, the tube is cut away and the remainder of the skirt can be left implanted or removed. All the different constructions shown in U.S. Pat. No. 5,527,317 can be incorporated into the tube used in the method described herein. It will thus be appreciated that the tube acts as a loading and guide tube for the cup. The construction of a profile gauge which forms the subject of the present invention is shown in FIGS. 8 to 12.

The gauge 20 comprises adjustable rods or pins for measuring and indicating the diametric profile of the rim 2 of the acetabular socket and includes a body portion formed by a substantially circular annulus 21 which can be of a plastics material or metal. Mounted in the annulus is a series of peripherally projecting indicators provided by radially extending rods or pins 22 which are oriented so that they provide a dished configuration. The pins 22 are held by friction as a relatively tight sliding fit in the annulus 20 so that they can be pushed in and out radially from one end or the other to define the shape of the rime of the socket as explained hereunder and so that the pins hold their position during removal of the gauge form the patient during the process of transferring the profile.

The body portion provided by the annulus 21 also carries a ring of locating rods 23, the ends 24 of which project outwardly from a flat surface 25 of the annulus and provide part of the means for accurately locating the measuring means in relation to the mouth of the socket to be measured. The other ends 26 of the rods 23 project from an opposed flat surface of the annulus and provide part of the means for removably locating the adjustable means provided by the annulus 21 or the pins 22 on the loading tube 31.

It will be appreciated that there are numerous ways of constructing the gauge, for example, it could be of two parts which are held together by the rods 23. Again, the annulus itself could be dished with the radial pins 22 being aligned within it.

A construction could also be devised in which the pins 22 are not dished, but merely project radially outwardly, although dishing is a convenient construction. Again, the angle of dishing around the gauge could vary to match the angle of the skirt on the tube or flange on the cup to be used.

FIGS. 10, 11 and 12 show how the profile gauge is used. The same reference numerals are used in FIGS. 10 and 11 to indicate parts shown in FIGS. 1 to 7. The means for accurately locating the adjustable means in relation to the rim of the socket to be measured include the trial cup 5 and a cup plug 27 which can be located in the trial cup 5 and which has a ring of sockets 28 into which the ring of rods 23 can fit to hold the annulus 20 accurately in position.

With the adjustable means held in this way the pins 22 are pushed outwardly until they engage the rim 2 of the socket to thus provide the shape of an outline. The provision of the openings 35 in the annulus 21 provides access to the inner ends of the pins 22.

FIG. 11 shows how the surgeon can record the profile over the top of the rim, which in this case is formed on one side by the morselized bone grafting 3.

The plug 27 is now removed complete with the adjustable means and the ends 26 of the rods 23 are pushed into a loading tube plug 29 which is adapted to engaged and fit within the bore 36 of the loading tube 31. The plug 29 is pushed into the bore until the pins 22 engage the skirt 30 and the shape thus defined thereon can either be marked or the skirt can be trimmed by the surgeon with the adjustable means in place.

If desired, the cup plug 27 can be removed before inserting the plug 29 into the bore 36 of the tube 31.

It will be seen that the dished configuration of the projecting indicators provided by the pins 22 ensure that they are substantially parallel to the projecting angle of the skirt 30 on the loading tube 31 with which they are to be used.

The cement mantle will be typically 3 mm all around the implanted cup. The cup need have no integral flange. Therefore the 3 mm cement thickness will be generated by a 1 mm tube wall thickness plus 2 mm of tube skirt (plus additional skirt depth which might overlay any bone grafting).

If the skirt is to overlay any bone grating the shape of the skirt can be cut slightly larger than that indicated by the pins 22 at that point or it can be measured as shown in FIG. 11.

Figure 13:
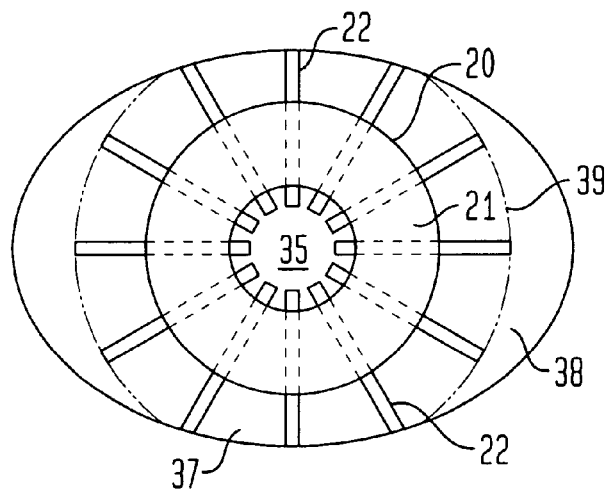
FIG. 13 is a diagrammatic plan view showing how a profile gauge of the kind according to the invention can be used to transfer the dimensions of an acetabular opening to a flanged cup to enable the flanges thereon to be cut to shape.
Figure 14:
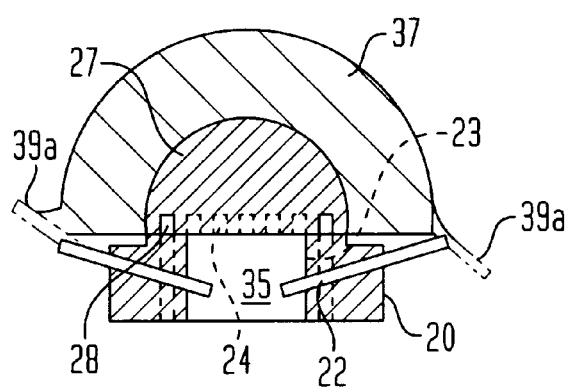
FIG. 14 is a diagrammatic side view of the gauge as applied to a flanged cup.
Figure 15:
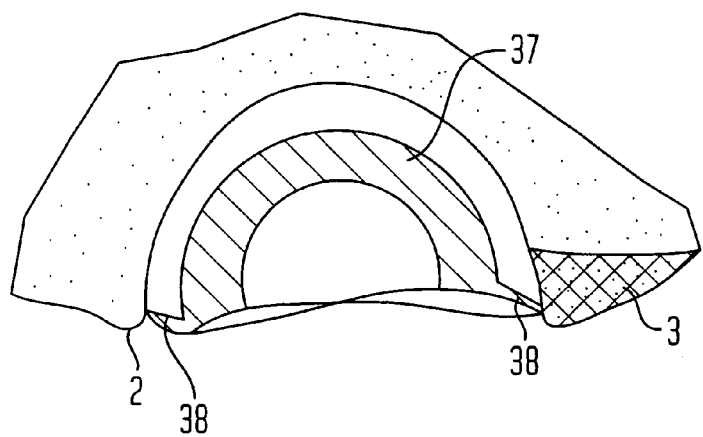
FIG. 15 is a diagrammatic side elevation of a flanged cup in position in an acetabular socket.

FIGS. 13 to 15 show a modified form of profile gauge according to the invention which can be used to measure and indicate the diametric profile of an acetabular socket and which can be used to transfer the shape to the flange of a flanged type acetabular cup so that the flange can be cut to accurately engage within the socket. In this construction the same reference numerals are used to indicate similar parts to those in FIGS. 8 to 12.

Flanged acetabular cups are known and are held in place in the acetabular socket by cement. In FIGS. 13 and 14 the flanged acetabular cup is indicated by reference numeral 37 and its flange by reference numeral 38. The flange is usually supplied as an oversize shape and is then cut to fit the rim 2 of the acetabular socket.

In some flanged cup constructions (for example, of the type shown in U.S. Pat. No. 4,327,449) the cup flanges have a varying angle of dishing around the circumference in which case the dishing angle of the pins 22 can also be varied to suit the type of cup with which the gauge is to be used.

The profile gauge is initially used to measure the rim of the socket in the manner shown in FIG. 10, that is by employing a trial cup and using a cup plug 27. When the pins 22 have been moved to their positions, the cup plug is removed and placed in the socket of the flanged cup 37 as shown in FIG. 3. The shape of the required flange is now indicated, as shown in FIG. 13, where the desired shape is indicated by broken line 39. The line can either be marked or the flange can be trimmed by the surgeon with the gauge in situ. The parts of the flange which are removed are indicated in FIG. 14 by reference numeral 39a. With the flange cut to shape, the cup can now be inserted into the prepared acetabular socket and held by cement as shown in FIG. 15.

It will be appreciated that he gauge can be used without a trial cup by being freely held in position whilst the pointers are adjusted. Preferably, however, the acetabulum is filled with something on which the gauge can locate.

In FIG. 15 a bone grafted portion 3 is shown, but the process and gauge can, of course, be employed with cups for use with flanged cups for use in sockets which are in better condition. As will be seen from FIG. 14, the gauge includes locating rods 23 which have projecting upper portions 24. In this construction, however, the lower portions can be deleted.

If, however, the gauge was designed exclusively for use with flanged cups, then the lug 27 could be incorporated into the main body portion 20 and the pins 23 would not be required.

Any sort of eccentricity of the cup or the flange can be catered from, for example, the flange of a cup shown in U.S. Pat. No. 4,327,449, an eccentric bearing surface within the cup, or a Charnley high posterior wall design (U.S. Pat. No. 3,722,002), where the chamfered entry to the cup bearing surface is interrupted, leaving a posteriorly placed ledge. In order to assist in use, a colored pin or a larger pin or some other circumferential marker can be used which will enable the surgeon to circumferentially match the profile gauge with the flange before trimming. This applied to both cup flanges and tube skirts.

Figure 16:
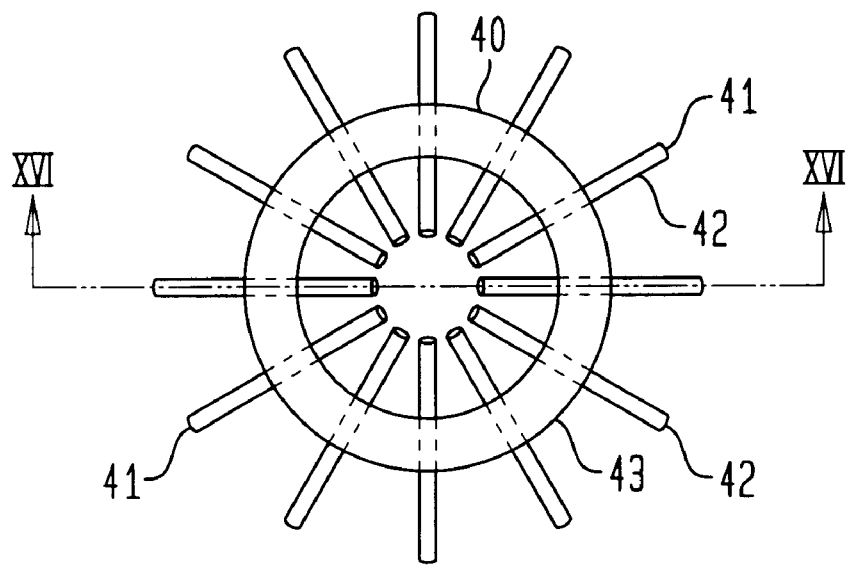
FIG. 16 is a plan view of a profile gauge which can be used for a bone opening, for example, for measuring the diametric profile of the medullary canal of a tibia.

FIG. 16 shows a profile gauge for measuring and indicating a diametric profile of a bone opening and which is constructed in a somewhat similar manner to that described with regard to FIGS. 8 to 12. Thus, the device comprises a substantially circular body portion 40 and a number of peripherally projecting indicators 41. Each indicator is in the form of a radially extending pin 42, the outer end of which projects beyond the outer rim 43 of the main body portion 40 and the inner end of which extends upwardly to provide an operating handle 44 as is most clearly shown in FIG. 17.

The center portion 45 of the main body portion is recessed to provide an upwardly projecting rim 46 in which the pins 42 are located. The pins 42 are held by friction as a relatively tight sliding fit in the rim portion 46 so that they can be pushed in and out radially by means of the handles 44 to define the shape of the opening in which they are placed.

In FIG. 13 the gauge is located in a medullary canal indicated by reference numeral 47 and if desired a centralizing plug indicated by chain lines 48 can be provided, the plug being attached by any convenient means to the main portion 40.

Alternatively, the plug could be incorporated into the main body portion 40 as required.

Figure 17:
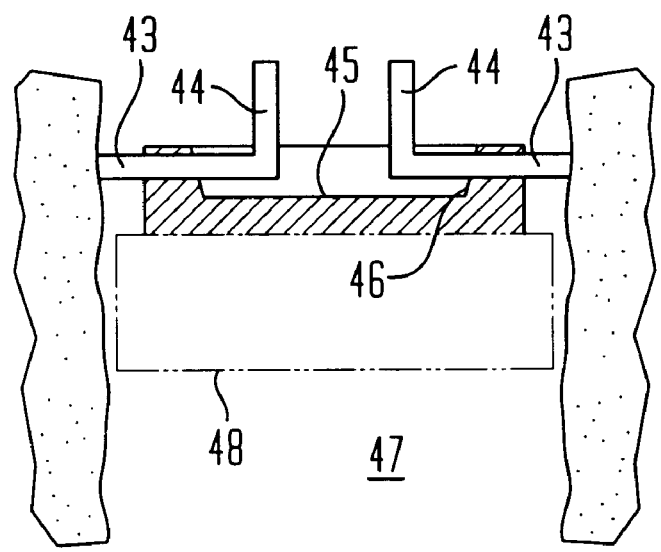
FIG. 17 is a cross-sectional side elevation on the line XVI—XVI of the device shown in FIG. 16 in place in a medullary canal.

In the construction shown in FIGS. 16 and 17 the main body portion 40 is circular, but it could be any convenient shape, for example rectangular, triangular, elongated or oval, depending upon the particular use for which the gauge was required. The projecting indicators could be angled in the main body portion to provide a disc configuration if this was more convenient for the requirement.

In an alternative construction the profile gauge could be substantially as shown in FIGS. 8 and 9 with or without means for attaching it to other members for centralization, that is the main body portion could be annular but of any convenient shape in plan view.

While several examples of the present invention have been described, it is obvious that many changes and modifications may be made thereunto, without departing from the spirit and scope of the invention.

We claim:

1. A profile gauge for use with a prosthetic acetabular cup which has skirt or flange connected thereto which can be trimmed and which is adapted to cooperate with the periphery of an opening in the acetabulum, said profile gauge comprising an adjustable element for measuring and indicating the diametric profile of a mouth of a rim area adjacent to the acetabulum opening, said adjustable element allowing the indication on the skirt or flange the measure diameter profile, the adjustable element includes a body portion and a number of peripherally projecting indicators which can be adjusted to define the shape of the mouth of the opening in the acetabulum, said indicators are provided by axially movable pins.

2. The profile gauge as claimed in claim 1 wherein the device is an acetabular cup loading tube provided with a skirt, said bone opening is an acetabular socket and said adjustable means are adapted to measure and indicate the diametric profile of the mouth of the rim area adjacent thereto of said acetabular socket into which an acetabular cup is to be implanted.

3. The profile gauge as claimed in claim 1 wherein the device is a flanged acetabular cup, said bone opening is an acetabular socket and the adjustable means are adapted to measure and indicate the diametric profile of the mouth of the rim area adjacent thereto of said acetabular socket into which said acetabular cup is to be implanted.

4. The profile gauge as claimed in claim 1 wherein said pins are held in place by friction between each pin and the body portion.

5. The profile gauge as claimed in claim 1 wherein said body portion is substantially annular, the indicators projecting outwardly from the periphery thereof and also inwardly into a central opening.

6. The profile gauge as claimed in claim 2 wherein the means for removably locating said adjustable means includes a plug adapted to engage and fit within the bore of the loading tube with which the gauge is to be used.

7. The profile gauge as claimed in claim 6 wherein said plug is removable from said adjustable means.

8. The profile gauge as claimed in claim 1 further including means for axially locating the gauge in relation to the mouth of the bone opening to be measured.

9. The profile gauge as claimed in claim 8 wherein the bone opening locating means includes a trial acetabular cup.

10. The profile gauge as claimed in claim 9 further including a cup plug which can be located on or in said trial cup and to which the adjustable means is connected.

11. The profile gauge as claimed in claim 10 wherein the connection between the cup plug and the adjustable means is detachable.

12. The profile gauge as claimed in claim 1 wherein said projecting indicators have a dished configuration adapted to be substantially parallel to a projecting angle of the skirt on the loading tube or the flange of the flanged cup with which they are to be used.

13. A profile gauge for intra-operatively measuring and indicating a diameteric profile of an opening in the acetabulum or a rim area adjacent thereto for sizing a skirt connected to an acetabular cup, said gauge comprising a body portion and a number of peripherally projecting indicators which can be adjusted to define the profile or the rim area adjacent thereto of the opening in the acetabulum to be measured, said indicators are provided by axially movable pins, said pins are held in place by friction between each pin and the body portion, said body portion is substantially annular, the indicators projecting outwardly from the periphery thereof and also inwardly into a central opening.

14. The profile gauge as claimed in claim 13 wherein said projecting indicators have a dished configuration adpated to be substantially parallel to a projecting angle of a skirt on a loading tube or a flange of the flanged cup with which they are to be used.

15. A profile gauge for intra-operatively measuring and indicating a diameteric profile of an opening in the acetabulum or a rim area adjacent thereto for sizing a skirt connected to an acetabular cup comprising a body portion and a number of peripherally projecting indicators which can be adjusted to define the profile or the rim area adjacent thereto of the opening in the acetabulum to be measured, said indicators are provided by axially movable pins.

16. A profile gauge for intra-operatively measuring and indicating a diametric profile of a bone opening in the acetabulum or a rim area adjacent thereto for sizing an implant on a skirt connected to an acetabular cup comprising a body portion and a number of peripherally projecting indicators which can be adjusted to define the profile or the rim area adjacent thereto of the opening in the acetabulum to be measured said indicators are provided by axially movable pins and said pins are held in place by friction between each pin and the body portion.

* * * * *

UNITED STATES PATENT AND TRADEMARK OFFICE
CERTIFICATE OF CORRECTION

PATENT NO. : 6,197,032 B1
DATED : March 6, 2001
INVENTOR(S) : Lawes et al.

It is certified that error appears in the above-identified patent and that said Letters Patent is hereby corrected as shown below:

Column 3,
Line 66, "shown" should read -- show --.

Column 4,
Line 6, after "that is" insert -- , --.
Line 40, "rime" should read -- rim --.

Column 5,
Line 31, after "grating" insert -- , --.

Column 6,
Line 1, "he" should read -- the --.
Line 26, after "This" insert -- is --.
Line 62, after "is" insert -- , --.

Column 8,
Line 38, after "thereto" insert -- on a skirt connected to an acetabular cup --.
Line 39, cancel "on a skirt connected to an acetabular cup".
Line 43, after "measured" insert -- , --.

Signed and Sealed this

Twentieth Day of November, 2001

*Attest:*

Nicholas P. Godici

*Attesting Officer*

NICHOLAS P. GODICI
*Acting Director of the United States Patent and Trademark Office*